United States Patent [19]

Shu et al.

[11] Patent Number: 5,424,214

[45] Date of Patent: Jun. 13, 1995

[54] DILUENT AND METHOD FOR DETERMINATION OF TOTAL CALCIUM

[75] Inventors: Frank R. Shu, Hacienda Heights; Xihai Mu, Chino Hills; Suzanne C. Chung, Brea; Peter J. Houben, Yorba Linda; James T. Kessler, Anaheim, all of Calif.

[73] Assignee: Beckman Instruments, Inc., Fullerton, Calif.

[21] Appl. No.: 144,928

[22] Filed: Oct. 27, 1993

Related U.S. Application Data

[63] Continuation-in-part of Ser. No. 826,284, Jan. 24, 1992, abandoned, which is a continuation of Ser. No. 592,768, Oct. 3, 1990, abandoned.

[51] Int. Cl.$^6$ ............................................. G01N 33/20
[52] U.S. Cl. ........................................ 436/74; 436/79; 436/151; 436/176; 436/179
[58] Field of Search ................ 436/74, 79, 73, 149, 436/150, 151, 176, 179; 73/1 R

[56] References Cited

U.S. PATENT DOCUMENTS

| | | | |
|---|---|---|---|
| 3,424,688 | 1/1969 | Boiko et al. | 252/87 |
| 3,934,977 | 1/1976 | Cleaver | 436/74 |
| 4,363,633 | 12/1982 | Christiansen | 436/19 |
| 4,404,040 | 9/1983 | Wang | 134/22.14 |
| 4,496,470 | 1/1985 | Kapiloff et al. | 252/181 |
| 4,618,587 | 10/1986 | Premoli et al. | 436/74 |
| 4,724,216 | 2/1988 | Young et al. | 436/79 |
| 4,793,942 | 12/1988 | Lakkesmoe et al. | 252/99 |
| 4,870,024 | 9/1989 | Musacchio et al. | 436/74 |
| 4,871,678 | 10/1989 | Wahl et al. | 436/79 |
| 4,945,062 | 7/1990 | Chiang | 436/11 |

FOREIGN PATENT DOCUMENTS

| | | |
|---|---|---|
| 0166944 | 5/1985 | European Pat. Off. |
| 0203334 | 4/1986 | European Pat. Off. |
| 0319863A3 | 3/1988 | European Pat. Off. |
| 0304151 | 4/1988 | European Pat. Off. |
| 2147066 | 9/1971 | Germany |
| WO89/12827 | 5/1989 | WIPO |

OTHER PUBLICATIONS

CRC Handbook of Chemistry and Physics, 63rd Edition, 1982-83 D156.
Development of a Method of Analysis . . . , Clinical Chemistry, vol. 34, No. 6, 1988, 1184-1186.
Non-selective Determination of Total Metal Ion Concentration in an excess of complexing Ligand Using the Standard Additions Method, Analyst, Apr. 1985, vol. 110, 359-363.
Direct Potentiometric Determination of Calcium in Waters with a constant Complexation Buffer, Analytica Chimica Acta, 68 (1974), 155-160.
Potentiometric Method for the Determination of Calcium in Blood Serum, Analytica Chimica Acta, 233 (1990) 269-273.
A New Instrument for the Clinical Determination . . . Mulholland, L., et al., Clin. Chem., 30:961 (1984).

*Primary Examiner*—Lyle A. Alexander
*Assistant Examiner*—Rachel Heather Freed
*Attorney, Agent, or Firm*—William H. May; Arnold Grant; Sheldon & Mak

[57] ABSTRACT

Diluents and methodologies for determining the concentration of total calcium in a clinical sample (e.g. whole blood, sera plasma urine cerebro spinal fluid) containing protein-bound calcium are disclosed. Methodologies include the steps of: (a) admixing the sample with a diluent, the diluent including effective amounts of a pH buffer and at least two agents capable of complexing free calcium in the sample, where the agent-calcium complex association constants ("log K" in base 10) each have a range from about 1.5 to about 7.0; and (b) contacting an aliquot of the diluted sample with a calcium-specific ion selective electrode. The response of the calcium-specific ion selective electrode is an indication of the concentration of total calcium in the sample.

23 Claims, No Drawings

DILUENT AND METHOD FOR DETERMINATION OF TOTAL CALCIUM

This application is a continuation-in-part application of U.S. application Ser. No. 07/826,284 filed Jan. 24, 1992, now abandoned, which is a file wrapper continuation of U.S. application Ser. No. 07/592,768 file Oct. 3, 1990, now abandoned.

FIELD OF THE INVENTION

The present invention is related to indirect potentiometric methodologies and diluents and particularly to a diluent useful in the indirect potentiometric determination of total calcium in clinical samples of bodily fluids.

BACKGROUND OF THE INVENTION

Calcium, the fifth most abundant element in the human body, plays an important physiological role and is essential for both the functional integrity of the nervous and muscular systems as well as normal cardiac function. Calcium is also one of the factors that operates in the mechanisms involved in the coagulation of the blood. More than 90% of the calcium in the human body is in the skeleton as calcium phosphate and calcium carbonate—the remainder of calcium is present in plasma. Plasma calcium levels vary from between about 9.0 and about 11.0 mg/100 mL. On average, about 46% is bound to protein; slightly more is free and ionized; and the remainder is freely diffusible but complexed and ionized. Total calcium, or "CAT" is the combined value of bound calcium ("CAB") free calcium ("CaF" or "Ca++") and protein complexed calcium ("CAP"), or:

$$CaT = CaB + CaF + CaP$$

CaF is generally accepted as being the physiologically active form of calcium in sera. Potentiometric sensors in the form of ion selective electrodes are useful in the determination of CaF.

Ion selective electrode technology involves the use of a reference electrode and an ion selective electrode ("ISE") separated by a membrane which are simultaneously immersed in a sample of a solution containing the desired ion. This simultaneous immersion leads to a potential across the membrane between the electrodes, which potential is proportional to the presence of the desired ion. Most often the investigator desires to only measure the concentration of one ion out of many different ions in solution. Thus, the composition of the ion selective electrode ISE must be capable of transporting the desired ion across the membrane in preference to all other ions which may be present. Two methodologies are associated with ISE technology: direct, where the sample is analyzed directly; and indirect, where the sample is diluted prior to analysis.

Conventional calcium ISE's only measure the free form of calcium. Accordingly, calcium indirect ISE methodologies employ diluents to displace the protein bound to calcium in an attempt to obtain an accurate reading of free calcium. Such conventional methodologies typically make use of strongly acidic diluents prior to ISE measurement in order to denature proteins bound to the calcium, that is, to displace or, "release", the bound calcium[1]. However, some ions, such as citrate (normally present in human sera at a level of about 0.1 mMol/L but during blood transfusions can be present in levels up to about 5 mMol/L), remain effective in binding calcium even under such acidic conditions[2]. Additionally, certain calcium ionophores will not function properly under such acidic conditions. Other methodologies have been described for releasing bound calcium[3], [4], [5], [6]. All of the preceding references of this paragraph are incorporated herein by reference.

Because of the problems associated with denaturing proteins bound to calcium in clinical samples, a diluent that does not rely upon denaturation and that does not utilize conditions which have an adverse affect upon the calcium ISE, as well as analytical methodologies employing such diluents, are desirable and would be of great value in the determination of total calcium in a clinical sample.

SUMMARY OF THE INVENTION

The present invention satisfies these requirements. The invention discloses diluents and methods for determining the concentration of total calcium in a clinical sample containing protein-bound calcium. A method of the present invention includes admixing the clinical sample with a diluent which includes an agent capable of forming an agent-calcium complex having a association constant of between about 1.5 and about 7. The concentration of the agent in the diluent is an amount sufficient to provide the diluted clinical sample with a constant free calcium mole fraction of from about 0.01 to about 0.025. Then contacting the diluted sample with a calcium specific ion selective electrode and measuring the response of the calcium specific electrode provides an indication of the concentration of total calcium in the clinical sample. In one embodiment, a method of the present invention includes admixing the sample with a diluent having effective amounts of a pH buffer and at least two agents capable of complexing free calcium in the sample, where the resultant agent-calcium complex association constants each have a range from about 1.5 to about 7.0; and contacting an aliquot of the diluted sample with a calcium-specific ion selective electrode.

In one embodiment of the present invention in which two complexing agents are utilized, at least one of the calcium complexing agent is also a pH buffer. For example, a diluent can include the calcium complexing agents, dibasic phosphate ($HPO_4$) and citrate ($(HO)C_3H_4(CO_2)_3$), wherein the pH buffer in the diluent is phosphoric acid in the form of approximately equal molar amounts of monobasic phosphate ($H_2PO_4$) and dibasic phosphate ($HPO_4$). This results in a diluent buffered to a pH of about 7.0. The pH of the diluent is preferably within the range of about pH 5.0 to about pH 8.5; most preferably, the pH of the diluent is about pH 7.0. Typically, the concentration of the pH buffer in the diluent is at least about 0.1 mole per liter and depending upon the agent-calcium association constant, the concentration of complexing agent in the diluent is typically at least about 0.002 moles per liter.

The diluent can further comprise other optional ingredients such as preservatives and surfactants. The volume to volume ratio of the clinical sample to the diluent is between about 1:10 and about 1:40, and most preferably this volume to volume ratio is about 1:20.

Because the diluent does not include harsh compounds to denature proteins bound to the calcium, the diluent can be used in association with conventional and commercially available calcium-specific ion selective electrodes.

DETAILED DESCRIPTION OF A PREFERRED EMBODIMENT

The diluent for measuring total calcium in a clinical sample includes therein effective amounts of agent capable of complexing free calcium in the clinical sample. As used herein, the term "complexing agent" is synonymous with "metal ion buffer". In order to be effective, the resultant agent-calcium complex association constant ("log K" in base 10) has a range of from about 1.5 to about 7.0; most preferably, this range is from about 2.0 to about 4.0.

Association constants can be derived from the stability constant ("K") of the complexing agent; the stability constants for a variety of such agents can be readily obtained from published sources. See, for example, Sillen & Martell, *Stability Constants Special Publication No. 17* London: The Chemical Society, Burlington House, London, England (1964), and Sillen & Martell, *Stability Constants, Supplement No. 1 Special Publication No. 25* London: The Chemical Society, Burlington House, London England (1971), which are incorporated herein by reference. For example, a measured association constant for calcium-dibasic phosphate is 2.74; a measured association constant for calcium-citrate is 3.60.

Dilution of a clinical sample, e.g., serum, plasma, whole blood, urine, cerebro spinal fluid, with a diluent including therein, for example, two agents capable of complexing free calcium, equilibrates the protein and other clinical sample compounds bound to the calcium (collectively "CAP") and agents bound to the calcium ("CaA" and "CaA'") as follows:

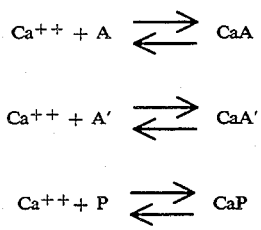

For convenience, charge symbols for A, A' and P are not included. Under the above criteria, total calcium concentration of the diluted sample for two complexing agents can be defined as:

$$[Ca^{++}] + [CaA] + [CaA'] + [CaP].$$

Accordingly, at equilibrium, the mole fraction ("R") of the free calcium ion can be expressed as follows:

$$R = \frac{[Ca^{++}]}{[Ca^{++}] + [CaA] + [CaA'] + [CaP]} \quad (1)$$

It is to be understood that additional agents can be utilized such that each additional agent (e.g. CaA") is similarly represented in Equation 1. Similarly, it is understood that one agent can be utilized, making equation (1) read as follows:

$$R = \frac{[Ca^{++}]}{[Ca^{++}] + [CaA] + [CaP]}$$

Equation (1) reduces to:

$$R = \frac{1}{1 + \frac{[CaA]}{[Ca^{++}]} + \frac{[CaA']}{[Ca^{++}]} + \frac{[CaP]}{[Ca^{++}]}} \quad (2)$$

By choosing agents that satisfy the relationship:

$$\frac{[CaA]}{[Ca^{++}]} + \frac{[CaA']}{[Ca^{++}]} + \ldots >> \frac{[CaP]}{[Ca^{++}]} \quad (3)$$

Equation 2 reduces to $$R = \frac{1}{1 + \frac{[CaA]}{[Ca^{++}]} + \frac{[CaA']}{[Ca^{++}]} + \ldots} \quad (3a)$$

In effect, the agents capable of complexing with free calcium are used to mediate or "control" the mole fraction of free calcium such that the amount of protein-bound calcium becomes inconsequential, as indicated in Equations 3 and 3a.

R can be expressed as a percentage of free calcium, i.e., $R \times 100\%$, and $[100\% - (R \times 100\%)]$ is defined as the value of the total mole percentages of the agent-calcium complexes, assuming that Equation 3 is satisfied. It is useful to first determine a value for one of the agent-calcium complexes such that the other agent-calcium complex(es) has that same value, such that $$\frac{[CaA]}{[Ca^{++}]} = \frac{[CaA']}{[Ca^{++}]}.$$

However, these values need not be equal; the critical requirement is that Equation 3 is satisfied when the values for the agent-calcium complexes are inserted into Equation 3. As such, less complexing agent can be added to the diluent than the amount actually calculated as long as the lesser amount would continue to satisfy Equation 3.

Additionally, it is useful to obtain values for $$\frac{[CaA]}{[Ca^{++}]} \text{ and } \frac{[CaA']}{[Ca^{++}]}$$

such that when incorporated into Equation 3a, R is a relatively small value, the proviso being that if R has too small a value, the calcium concentration of the sample can be difficult to measure with a calcium specific ion selective electrode and if R has too great a value, the agents become ineffective in maintaining a constant mole fraction of free calcium.

The selection of the range of R values is directly related to the volume to volume ratio of the sample to the diluent. For a 1:20 dilution ratio, R is preferably within the range of from about 0.009 to about 0.03, more preferably within the range of from about 0.01 to about 0.02, and most preferably about 0.012. As the dilution ratio decreases, the value range for R will decrease, and as the dilution ratio increases, the value range for R will increase. Thus, for a dilution ratio of 1:10, R is preferably within the range of from about 0.0025 to about 0.025; for a dilution ratio of 1:40, R is preferably within the range of from about .01 to about 0.10.

For a 1:20 dilution ratio, and utilizing a most preferred value for R of 0.012, Equation 2 can be expressed as follows:

$$.012 = \frac{1}{1 + \frac{[CaA]}{[Ca^{++}]} + \frac{[CaA']}{[Ca^{++}]} + \frac{[CaP]}{[Ca^{++}]}} \quad (2)$$

As previously noted, Equation 2 can be rewritten as Equation 3a when Equation 3 is satisfied. For most clinical samples, it is laborious to determine a value for $$\frac{[CaP]}{[Ca^{++}]}$$

because all of the stability constants for all proteins and other compounds that bind to calcium in the sample are tedious and/or difficult to determine. However, because the complexing agents are used to control the mole fraction of free calcium, a value for $$\frac{[CaP]}{[Ca^{++}]}$$

can, for practical purposes, have an assigned approximation value of less than or equal to 1.0. With respect to serum, this value can be empirically estimated using Human Serum Albumin, which is the dominant protein species in serum.

Because Human Serum Albumin ("HSA") is the dominant protein species in serum, a value for $$\frac{[CaP]}{[Ca^{++}]}$$

can be equated with a value for $$\frac{[CaHSA]}{[Ca^{++}]}.$$

At normal serum levels, HSA has a concentration of approximately 0.6 mMole/L. Assuming a 1:20 dilution ratio, and using the association constant model for the calcium—complex in human serum set forth in Fogh-Anderson, N. "Albumin/calcium association at different pH, as determined by potentiometry" *Clin. Chem.* 23:2122–2126 (1977), $$\frac{[CaHSA]}{[Ca^{++}]} = 0.3.$$

Accordingly, when $$\frac{[CaA]}{[Ca^{++}]} = \frac{[CaA']}{[Ca^{++}]} \gg 0.3,$$

Equation 3a is utilized to determine the concentration of the agents to be added to the diluent.

Assuming R to be equal to 0.012, and further assuming that $$\frac{[CaA]}{[Ca^{++}]} = \frac{[CaA']}{[Ca^{++}]}$$

then $$0.012 = \frac{1}{1 + (2x)}$$

-continued $$0.012 + .012(2x) = 1$$

$$012(2x) = .988$$

$$x = 41$$

Accordingly, $$\frac{[CaA]}{[Ca^{++}]} = \frac{[CaA']}{[Ca^{++}]} = 41$$

These values satisfy Equation 3 (82>>0.3). Because the value "82" is much greater than 0.3, it is possible to use less of each agent or less of one agent whereby Equation 3 is still satisfied. From a commercial standpoint, this is of beneficial value in that for a particularly strong calcium complexing agent, that is, one having a stability or association constant indicative of a strong calcium complexing agent, less of the agent can be used without compromising the importance thereof in the diluent. Similarly, as discussed below, Equation 3 is satisfied when only one agent is utilized at a concentration sufficient to provide the appropriate constant mole fraction of calcium. Preferably, when only one agent is utilized its agent-calcium association constant is relatively high in order to keep the concentration reasonably low.

In the case of using two agents ([A] and [A']) and in order to determine a useful concentration of the agents, the stability constants (K) are utilized as follows:

$$K = \frac{[CaA]}{[Ca^{++}] \times [A]}$$

$$K \times [A] = \frac{[CaA]}{[Ca^{++}]}$$

$$[A] = \frac{\frac{[CaA]}{[Ca^{++}]}}{K}$$

As set forth above, for $$\frac{[CaA]}{[Ca^{++}]} = 41,$$

then:

$$[A] = \frac{41}{K}$$

The association constant of the agent-calcium complex is preferably within the range of about 1.5 to about 7.0, with a most preferred range of from about 2.0 to about 4.0. Calcium-dibasic phosphate, at pH 7.0, has a measured association constant of 2.74; calcium-citrate, at pH 7.0, has a measured association constant of 3.60. Accordingly $$[\text{Dibasic phosphate}] = \frac{41}{10^{2.74}} = 0.075M$$

$$[\text{Citrate}] = \frac{41}{10^{3.60}} = .010M$$

As mentioned above, preferably a calcium complexing agent utilized in the diluent also acts as a pH for the diluent. In the case of the just described diluent, the dibasic phosphate can also act as such a pH buffer. However, the molar value for dibasic phosphate represents only one-half of the necessary amount of phosphoric acid that must be added to the diluent in that at pH 7.0, the other form of phosphoric acid is monobasic phosphate in an amount which is approximately equal molar concentration as dibasic phosphate. Therefore, at pH 7.0, 0.15M phosphoric acid, or 0.075M dibasic phosphate and 0.075M monobasic phosphate, is utilized because of this factor. Since the amount of phosphate agent is doubled, the amount of citrate can be halved. Thus, and for the reasons noted above, under these conditions, 0.005M (5 mMol) citrate is sufficient.

Examples of suitable agents that satisfy the agent-calcium complex association constant requirements include: dicarboxylic acids; tricarboxylic acids; iminodiacetic acids; sulfonic acids; and organophosphoric acids. Specific agents include: aspartic acid; gluconic acid; succinic acid; oxaloacetic acid; propane-1,2,3-tricarboxylic acid; citric acid; maleic acid; iminodiacetic acid; N-methyliminodiacetic acid; 4,5-dihydroxy-1,3-benzenedisulfonic acid; glycerol-2-phosphate, disodium salt; N-(2-hydroxycyclohexyl) iminodiacetic acid; nitrilotriacetic acid; N'-(2-hydroxyethyl) ethylenediamine-N,N,N'-triacetic acid; ethylenediamine-N,N-diacetic acid; 8-hydroxyquinoline-5-sulfonic acid; nitric acid; and phosphoric acid.

The pH buffer is chosen such that the pH of the diluent is within the range of about pH 5.0 to about pH 8.5. Preferably, the pH of the diluent is about 7.0. Combinations of pH buffers can be utilized to satisfy these requirements. The pH buffer can comprise at least one of the following: acetic acid; 2-(N-morpholino)ethanesulfonic acid; 3-(N-morpholino) propanesulfonic acid; N-2-hydroxyethyl piperazine-N'-2-ethanesulfonic acid; phosphoric acid; N-[tris-(hydroxymethyl)methyl]glycine; diethynol amine; dimethylamine; phosphoric acid; tris(hydroxymethyl)aminomethane; and other alkyl amines.

For many calcium determination methods phosphate buffers are the buffers of choice. In view of their usefulness as a calcium complexing agent, phosphoric acid in the form of dibasic and monobasic phosphate is then the preferred pH buffer for diluent utilized in the present invention. The pH buffer has a concentration in the diluent of at least about 0.1 mole per liter, more preferably a concentration in the diluent of between about 0.1 mole per liter and about 0.4 mole per liter, and most preferably a concentration in the diluent of about 0.15 mole per liter. Other ingredients can be added to the diluent that do not affect the diluent and which are used in association with the pH buffer to balance the charge thereof. For example, when phosphoric acid is used as a pH buffer, it is useful to include in the diluent a "counter cation", i.e. an ingredient to balance the anionic charge of the phosphoric acid. For phosphoric acid, a suitable counter cation is tris(hydroxymethyl)aminomethane (hereinafter "TRIS").

For many automated clinical analyzers useful for the determination of calcium concentration and other sample analytes, the presence of phosphate can be an interfering functionality. Thus, in these cases pH buffers free of phosphate are preferred.

The diluent can also include therein a surfactant, the preferred surfactant being non-ionic, and more preferably 2,4,7,9-tetramethyl-5-decyn-4,7-diol. The foregoing surfactant is commercially available under the brandname Surfynol 104 TM (Air Products, Allentown, Pa.). A preservative can also be added to the diluent, such as, for example, phenoxyethanol.

An embodiment of the presently claimed diluent would include the following:

| Total Calcium Diluent | |
|---|---|
| Ingredient | Concentration |
| TRIS | 0.30 mole per liter |
| phosphoric acid | 0.15 mole per liter |
| citrate (citric acid) | 5 millimole per liter |
| 2,4,7,9-tetramethyl-5-decyn-4,7, diol | 0.02 per cent by weight |
| phenoxyethanol | 0.02 per cent by weight |
| pH of diluent | 7.0 |

It is to be understood that the foregoing description of an embodiment of the diluent is not to be construed as an indication that the complexing agents are limited to dibasic phosphate and citrate, or that the pH buffer and at least one of the complexing agents are the same. The preceding methodology can be advantageously utilized to determine other agents capable of complexing free calcium which can be added to the diluent for the analysis of clinical samples.

EXAMPLES

The following examples are presented for illustration purposes only and are not intended to limit the scope of the invention, the disclosure, or the claims that follow.

Analysis of various diluents for the determination of total calcium was performed on a modified SYNCHRON® EL-ISE TM analyzer (Beckman Instruments, Inc., Brea, Calif.), utilizing a calcium-specific ion selective electrode similar to that described in Reference 1, infra. Serum samples from healthy individuals were diluted one part sample volume to twenty parts diluent; dilution was automatically accomplished by the aforementioned analyzer prior to analysis. All chemicals used for testing were ACS grade, and were freshly prepared prior to analysis. Calcium standards were prepared from a stock solution including therein SRM 915 TM calcium carbonate.

Example I

Protein Effect on Calcium Recovery

The aforementioned serum pools were spiked with 5.0 g/dL Human Serum Albumin (Cohn Fraction V, Sigma Chemical Co., St. Louis, Mo.) for analysis of protein effect on calcium recovery. Differing amounts of the aforementioned calcium carbonate were added to the protein spiked serum samples. Comparisons were made between two diluents similar to that set forth as an embodiment of the diluent: the first included as a complexing agent only 0.15M phosphoric acid ("PA") and the second including both 0.15M phosphoric acid and 5 mmol citric acid ("PA/CA"). Normalized calcium recovery results (normalized against the calcium recovery values in the absence of HSA) derived from the indirect potentiometric analysis of the samples are presented in Table I:

TABLE I

| | Normalized Calcium Recovery | |
|---|---|---|
| | Diluent Agent | |
| Ca++ (mg/dl) | PA | PA/CA |
| 5 | .8667 | 1.0185 |
| 10 | .8713 | 0.9907 |
| 15 | .8782 | 0.9811 |

The results indicate that calcium recovery is significantly improved with the addition of citrate in the diluent.

EXAMPLE II

Citrate Effect on Calcium Recovery

Reference 1,infra, describes a 30% reduction in the recovery of total calcium with the presence of 1 mmol of citrate in serum samples. Increasing amounts of citrate were added to serum samples and the aforementioned diluents of Example I were tested. Normalized calcium recovery values are set forth in Table II:

TABLE II

| | Normalized Calcium Recovery | |
|---|---|---|
| | Diluent Agent | |
| Citrate (mmol) | PA | PA/CA |
| 0 | 1.00 | 1.00 |
| 1.0 | 1.00 | 1.00 |
| 5.0 | .97 | .99 |
| 10.0 | .93 | .97 |

The results set forth in Table II indicate that at the 1.0 mmol citrate level, complete calcium recovery was obtained when either of the tested diluents were utilized. However, at the 5.0 mmol citrate level, the citrate effect on calcium recovery was approximately 3% when only phosphoric acid was used as the complexing agent, while the citrate effect was significantly decreased when both phosphoric acid and citric acid were used as complexing agents. At the 10.0 mmol level, the citrate effect on calcium recovery was reduced by over 50% when both complexing agents were added to the diluent, compared to when only the phosphoric acid was added to the diluent.

EXAMPLE III

Correlation Study

Serum correlation studies were conducted between the indirect potentiometric analysis for total calcium recovery and the atomic absorption method for calcium recovery, using a Jerrel Ash Model 12E ™ AA Spectrophotometer. For the indirect potentiometric analysis, the diluent included both of the aforementioned agents, phosphoric acid and citric acid. Correlation results summarized as follows:

$$Y_{Indirect} = 1.0359 * X_{AA} - 0.3302$$

$$N = 97$$

$$R^2 = .9844$$

EXAMPLE IV

Determination of Calcium Concentration

Dilution of a clinical sample can effectively place the diluted sample-calcium concentration into the non-linear range of the calcium-specific ion selective electrode. As such, the diluent preferably includes therein calcium or a salt thereof in an amount effective to correct for a decrease in sensitivity of a calcium-specific ion selective electrode. This additional calcium or calcium salt is referred to as a "spiking factor" or "SF". Generally, and because of the objective thereof, the concentration of the SF added to the sample is relatively small, usually on the order of from about 0.015 mmol/L of diluent to about 0.035 mMol/L of diluent, and most preferably, about 0.02 mMol of calcium carbonate is added per liter of diluent.

When the diluent incorporates the SF therein, determination of calcium concentration in the clinical sample can be determined using the following modified Nicolskii-Eisenman equation:

$$C_{Ca} = \text{antilog } [(E_{Ca} - E^\circ)/S] - SF \quad (5)$$

where: $E_{Ca}$ is the value (in mV) of the calcium-specific ion selective electrode towards the calcium in the diluted sample; $E^\circ$ is a constant EMF difference (temperature dependent); S is the slope and the electrical response function; SF is the value of the amount of the spiking factor added to the diluent as well as a system "carry-over" value attributed to residual calcium which may remain on the calcium specific ion selective electrode or flow cell; and $C_{Ca}$ is the determined concentration of calcium in the clinical sample. If a SF is not utilized in the diluent, then the concentration of calcium in the clinical sample can be determined as follows:

$$C_{Ca} = \text{antilog } [(E_{Ca} - E^\circ)/S] \quad (6)$$

where the foregoing definitions apply.

For a preferred analysis of clinical samples for the determination of calcium therein, an automatic electrolyte system utilizing an indirect potentiometric methodology can be utilized, such as, for example, a SYNCHRON® EL-ISE ™ analyzer (Beckman Instruments, Inc., Brea, Calif.) although the invention is not to be limited in its applicability to this preferred analyzer.

Most preferably, a 50 uL clinical sample (e.g. serum) is diluted 20 fold with the most preferred diluent. For the analysis of the diluted sample, the aforementioned analyzer measures the calcium-specific ion selective electrode response this value is represented as $E_{Ca}$. Equations 5 or 6 can then be utilized to determine the value for $C_{Ca}$.

EXAMPLE V

As mentioned above, for many automated applications it is preferable to provide diluents free of phosphate. The following illustrates an exemplary diluent useful in embodiments of the present invention in which calcium concentration is determined in a phosphate free diluent.

A phosphate free diluent was prepared in an aqueous base and used to dilute a clinical sample for calcium concentration determination. The diluent includes the following components at the specified concentration in an aqueous base:

| | |
|---|---|
| Tris(hydroxymethyl)aminomethane | 1.0 Mol/L |
| Maleic Acid | 0.35 Mol/L |
| Citric Acid | 0.05 Mol/L |
| 2,4,7,9-tetramethyl-5-decyn-4,7-diol | 0.10 wt % |
| Glydant Plus (preservative) | 0.10 wt % |

A clinical sample was placed in a CX3 Delta Clinical Analyzer. The above described diluent was first diluted 1:4 with an aqueous based diluent and then the clinical sample was diluted 1:20 with the diluted diluent. The resulting diluted sample had a constant mole fraction free calcium of 0.02 or 2%. Calcium concentration was determined using a calcium ion specific electrode (ISE). The serum sample was then analyzed for calcium using atomic absorption. The results of calcium concentration determination with the ISE compared well with the results obtained with atomic absorption.

EXAMPLE VI

The following illustrates another exemplary diluent useful in embodiments of the present invention in which calcium concentration is determined in a phosphate free diluent.

A phosphate free diluent was prepared in an aqueous base and used to dilute a clinical sample for calcium concentration determination. The diluent includes the following components at the specified concentration in an aqueous base:

| | |
|---|---|
| Tris(hydroxymethyl)aminomethane | 0.25 Mol/L |
| Nitric Acid | 0.125 Mol/L |
| Citric Acid | 0.012 Mol/L |
| 2,4,7,9-tetramethyl-5-decyn-4,7-diol | 0.02 wt % |
| Phenoxyethanol (preservative) | 0.02 wt % |

A clinical sample was placed in a Vanguard Clinical Analyzer (Beckman Instruments, Fullerton, Calif.) and the above described diluent was utilized to dilute the clinical sample in the Vanguard analyzer at a dilution of 1:20. The resulting diluted clinical sample had a constant mole fraction free calcium of 0.02 or 2%. The diluted clinical sample was placed in contact with a calcium ion specific electrode and calcium concentration was determined in accordance with the present invention. The results compared favorably with calcium determinations obtained utilizing atomic absorption techniques (N=60, $R^2$=0.99, slope=0.965, intercept=−0.368).

EXAMPLE VII

The following example illustrates a calcium ion determination diluent which includes an additional surfactant in the form of a relatively high molecular weight water soluble polymer. The presence of this polymer reduces the adverse effect of protein serum on the surface of the ion specific electrode which simultaneously reduces the protein bias on the electrode. In this example the polymer is 6000 molecular weight polyethylene glycol (PEG 6000). However, other water soluble polymers including but now limited to polyvinylpyrrolidinone, polyvinyl alcohol, and polysaccharide based polymers. The diluent includes the following components at the specified concentration in an aqueous base:

| | |
|---|---|
| Tris(hydroxymethyl)aminomethane | 0.2 Mol/L |
| Maleic acid | 0.07 Mol/L |
| Polyethylene glycol (PEG 6000) | 2 wt % |
| Citric Acid | 0.010 Mol/L |
| Brij 35 wetting agent | 0.003 wt % |
| Phenoxyethanol (preservative) | 0.02 wt % |

(Brij 35 available from Aldrich Chemical is polyoxyethylene (23) lauryl ether.)

This diluent was used to dilute serum samples at a 1:20 dilution after which the calcium concentration in the serum was determined using a calcium ion specific electrode. The results were correlated with a Synchron ™ CX3 (available from Beckman Instruments, Fullerton, Calif.) colorimetric method. The correlation results were N=19, $R^2$=0.96, Slope=0.934, intercept=0.319.

EXAMPLE VIII

The following example illustrates a calcium ion determination diluent which further includes additives designed to improve the linearity of the calcium measurements. The diluent includes the following in an aqueous base:

| | |
|---|---|
| Maleic Acid | 0.368 M |
| tris(hydroxymethyl)aminomethane | 1.0 M |
| KCl | 0.15 mM |
| NaCl | 0.5 mM |
| $NaNO_3$ | 2.0 mM |
| $CaCl_2 \cdot 2H_2O$ | 0.10 mM |
| Glydant Plus | 0.03 wt % |
| Surfynol 104 | 0.88 mM |

The above-described diluent was diluted 1:5 with an aqueous system and then 1 part of a clinical sample (urine or serum) was diluted with 20 parts of diluted diluent prior to determining calcium concentration utilizing a calcium ion specific electrode. The results obtained with the ion specific electrode were compared with results obtained utilizing atomic absorption techniques. (A Jerrel Ash Model 12 E AA atomic absorption spectrophotometer was used to obtain the atomic absorption results.)

For serum samples the ion specific electrode correlated with the atomic absorption results as follows: Y=0.96X+0.3, N=57 R=0.97. For urine samples the results obtained with the ion specific electrode correlated with the atomic absorption results as follows: Y=0.97X−0.091, N=54, R=0.99.

EXAMPLE IX

The effect of calcium complex agent on the recovery of calcium was demonstrated using citrate as the complexing agent. The data shown below clearly evidence the effect of the complexing agent on total calcium recovery.

| Sample | % of Calcium recovery | |
|---|---|---|
| 8 mg/dL of Ca plus: | w/o agent[1] | w/ agent[2] |
| 1 mmol/L citrate | 97 | 102 |
| 5 mmol/L citrate | 76 | 94 |
| 10 mmol/L citrate | 61 | 86 |
| 3 wt % human serum albumin | 95[3] | 105[3] |
| 7.5 wt % human serum albumin | 89[3] | 104[3] |
| 12 wt % human serum albumin | 85[3] | 101[3] |

Notes:
[1]Tris(hydroxymethyl)aminomethane pH buffer at 0.6 Mol/L, pH 8.2.
[2]Tris(hydroxymethyl)aminomethane pH buffer at 0.51 Mol/L, maleic acid complexing agent at 0.17 Mol/L, pH 8.2.
[3]there was some background calcium in the human serum albumin which was not corrected for in the computation.

The above detailed working examples establish the excellent results obtained when utilizing the methods and diluents of the present invention to obtain calcium ion concentrations in clinical samples. More particularly, by controlling the free calcium ratio in the clinical sample, the methods of the present invention give reliable consistent calcium determination with ion specific electrodes. These results have been substantiated by their excellent correlation with atomic absorption techniques, a well established and reliable method for obtain calcium concentrations.

The above examples are of preferred embodiments of the disclosed invention. Modifications that are within the purview of those skilled in the art are intended to be within the scope of the invention.

BIBLIOGRAPHY

1. Anker, P. et al. "Neutral Carrier Based Ion-Selective Electrode for the Determination of Total Calcium in Blood Serum." *Anal. Chem.* 53:1970–1974 (1981).
2. Gawoski, J. M. and Walsh, D. "Citrate Interference in Assays of Total Calcium in Serum." *Clin. Chem.* 35:2140–2141 (1989)
3. U.S. Pat. No. 4,724,216
4. U.S. Pat. No. 3,934,977
5. U.S. Pat. No. 4,363,633
6. U.S. Pat. No. 4,870,024

What is claimed is:

1. A method for determining the concentration of total calcium in a sample, said method comprising the steps:
    (a) admixing said sample with a diluent to form a diluted sample, said diluent comprising a complexing agent which also serves as a pH buffer, said agent being capable of forming an agent-calcium complex, said agent-calcium complex having an association constant of between about 1.5 and 7 and being present in said diluent in an amount sufficient to provide said diluted sample with a constant free calcium mole fraction of from about 0.0025 to 0.1;
    (b) contacting said diluted sample with a calcium ion specific electrode; and
    (c) measuring the response of said calcium ion specific electrode to determine the calcium concentration in said sample.

2. The method of claim 1 wherein said diluted sample has a volume to volume ratio of said sample to said diluent of between about 1:10 and about 1:40.

3. The method of claim 1 wherein said complexing agent is capable of buffering said diluent to a pH of between about 5.0 and 8.5.

4. The method of claim 1 wherein said complexing agent is phosphoric acid having equal molar concentrations of phosphate (monobasic) and phosphate (dibasic).

5. The method of claim 1 wherein the diluent includes, in addition to the complexing agent, tris(hydroxymethyl)aminomethane as a pH buffer.

6. The method of claim 1 wherein the diluent includes, in addition to the complexing agent, a pH buffer selected from the group consisting of acetic acid; 2-(N-morpholino)ethanesulfonic acid; 3-(N-morpholino)propanesulfonic acid; N-2-hydroxyethyl piperazine-N'-2-ethanesulfonic acid; phosphoric acid; N-[tris(hydroxymethyl)methyl]glycine; diethynol amine; dimethylamine; tris(hydroxymethyl)aminomethane; and the alkyl amines.

7. The method of claim 1 wherein the association constant values of said agent-calcium complex is between about 2.0 and about 4.0.

8. The method of claim 1 wherein said diluent includes at least two complexing agents.

9. The method of claim 1 wherein the diluent includes an additional complexing agent selected from the group consisting of citric acid, maleic acid, nitric acid, hydroxyethyliminodiacetic acid, and phosphoric acid.

10. A method for the indirect potentiometric measurement of calcium in a sample, said method comprising the steps:
    (a) admixing said sample with a diluent to form a diluted sample, said diluent comprising at least two complexing agents capable of forming an agent-calcium complex, said diluent further including additives selected from the group consisting of preservatives, surfactants, and inorganic salts, each of said agent-calcium complexes having an association constant of between about 1.5 and 7 and the total amount of each of said complexing agents being sufficient to provide said diluted sample with a constant free calcium mole fraction of from about 0.009 to about 0.03;
    (b) contacting said diluted sample with a calcium ion specific electrode; and
    (c) measuring the response of said calcium ion specific electrode to determine the calcium concentration in said sample.

11. A method for the indirect potentiometric measurement of calcium in a sample, said method comprising the steps:
    (a) admixing said sample with a diluent to form a diluted sample, said diluent comprising i) at least two complexing agents capable of forming an agent-calcium complex, said complexing agents comprising about 0.125 Mol/L nitric acid, and about 0.012 Mol/L citric acid, each of said agent-calcium complexes having an association constant between 1.5 and 7 and the total amount of each of said complexing agents being sufficient to provide said diluted sample with a constant free calcium mole fraction from about 0.009 to about 0.03, ii) about 0.25 Mol/L tris(hydroxymethyl)aminomethane as a buffer, and iii) about 0.02 wt. % surfactant, and about 0.02 wt. % preservative;
    (b) contacting said diluted sample with a calcium ion specific electrode; and
    (c) measuring the response of said calcium ion specific electrode to determine the calcium concentration in said sample.

12. A method for the indirect potentiometric measurement of calcium in a sample, said method comprising the steps:
    (a) admixing said sample with a diluent to form a diluted sample, said diluent comprising i) at least two complexing agents capable of forming an agent-calcium complex, said complexing agents comprising about 0.35 Mol/L maleic acid, and about 0.05 Mol/L citric acid, each of said agent-calcium complexes having an association constant between 1.5 and 7 and the total amount of each of said complexing agents being sufficient to provide said diluted sample with a constant free calcium mole fraction from about 0.009 to about 0.03, ii) about 1.0 Mol/L tris(hydroxymethyl)aminomethane as a buffer, and iii) about 0.1 wt. % surfactant, and about 0.10 wt. % preservative, said method further including the step of diluting said diluent prior to admixing said sample and said diluent;
    (b) contacting said diluted sample with a calcium ion specific electrode; and
    (c) measuring the response of said calcium ion specific electrode to determine the calcium concentration in said sample.

13. The method of claim 10 wherein said diluent further includes pH buffer.

14. A method for the indirect potentiometric measurement of calcium in a sample, said method comprising the steps:
   (a) admixing said sample with a diluent to form a diluted sample, said diluent comprising at least two complexing agents wherein at least one of said complexing agents also serves as a pH buffer, said agents capable of forming an agent-calcium complex, each of said agent-calcium complexes having an association constant between 1.5 and 7 and the total amount of each of said complexing agents being sufficient to provide said diluted sample with a constant free calcium mole fraction from about 0.009 to about 0.03;
   (b) contacting said diluted sample with a calcium ion specific electrode; and
   (c) measuring the response of said calcium ion specific electrode to determine the calcium concentration in said sample.

15. A method for the indirect potentiometric measurement of calcium in a sample, said method comprising the steps:
   (a) admixing said sample with a diluent to form a diluted sample, said diluent comprising i) at least two complexing agents capable of forming an agent-calcium complex, said complexing agents comprising about 0.07 Mol/L maleic acid and about 0.010 Mol/L citric acid, each of said agent-calcium complexes having an association constant between 1.5 and 7, and the total amount of each of said complexing agents being sufficient to provide said diluted sample with a constant free calcium mole fraction from about 0.009 to about 0.03, ii) about 0.2 Mol/L tris(hydroxymethyl) aminomethane as a buffer, and iii) about 2 wt. % polyethyleneglycol 6000, and about 0.003 wt. % polyoxyethylene 23 lauryl ether.
   (b) contacting said diluted sample with a calcium ion specific electrode; and
   (c) measuring the response of said calcium ion specific electrode to determine the calcium concentration in said sample.

16. The method of claim 10 wherein said diluent is formed by diluting with water a composition comprising about 0.368 Mol/L maleic acid, about 1.0 Mol/L tris(hydroxymethyl)aminomethane, about 0.15 mMol/L KCl, about 2.0 mMol/L $NaNO_3$, about 0.5 mMol/L NaCl, and about 0.10 mMol/L $CaCl_2.2H_2O$.

17. A method for determining the concentration of total calcium in a sample, said method comprising the steps:
   (a) admixing said sample with a diluent to form a diluted sample, said diluent comprising (i) phosphoric acid and citric acid as complexing agents capable of forming an agent-calcium complex, said agent-calcium complex having an association constant between 1.5 and 7 and being present in said diluent in an amount sufficient to provide said diluted sample with a constant free calcium mole fraction of from about 0.0025 to about 0.1, and (ii) tris(hydroxymethyl)amine methane as a buffer, wherein the phosphoric acid serves as a buffer so that said diluent has a buffered pH of approximately 7;
   (b) contacting said diluted sample with a calcium ion specific electrode; and
   (c) measuring the response of said calcium ion specific electrode to determine the calcium concentration in said sample.

18. A method for determining the concentration of total calcium in a sample, said method comprising the steps:
   (a) admixing said sample with a diluent to form a diluted sample, said diluent comprising (i) maleic acid and citric acid as complexing agents capable of forming an agent-calcium complex, said agent-calcium complex having an association constant between 1.5 and 7 and being present in said diluent in an amount sufficient to provide said diluted sample with a constant free calcium mole fraction of from about 0.0025 to about 0.1, and (ii) tris(hydroxymethyl)amine methane as a buffer;
   (b) contacting said diluted sample with a calcium ion specific electrode; and
   (c) measuring the response of said calcium ion specific electrode to determine the calcium concentration in said sample.

19. A method for determining the concentration of total calcium in a sample, said method comprising the steps:
   (a) admixing said sample with a diluent to form a diluted sample, said diluent comprising (i) citric acid and nitric acid as complexing agents capable of forming an agent-calcium complex, said agent-calcium complex having an association constant between 1.5 and 7 and being present in said diluent in an amount sufficient to provide said diluted sample with a constant free calcium mole fraction of from about 0.0025 to about 0.1, and (ii) tris(hydroxymethyl)amine methane as a buffer;
   (b) contacting said diluted sample with a calcium ion specific electrode; and
   (c) measuring the response of said calcium ion specific electrode to determine the calcium concentration in said sample.

20. The method of claim 17, 18 or 19 wherein said diluted sample has a volume to volume ratio of said sample to said diluent between 1:10 and 1:40.

21. The method of claim 17, 18 or 19 wherein said pH buffer is capable of buffering said diluent to a pH between 5.0 and 8.5.

22. The method of claim 17, 18 or 19 wherein the association constant values of said agent-calcium complex is between 2.0 and 4.0.

23. The method of claim 17, 18 or 19 wherein said diluent includes at least two complexing agents.

* * * * *